United States Patent
Folsom et al.

(10) Patent No.: US 11,607,256 B1
(45) Date of Patent: Mar. 21, 2023

(54) BONE SCREW AND METHOD OF USING SAME

(71) Applicant: ALEVIO, LLC, Birmingham, AL (US)

(72) Inventors: Clint Folsom, Pelham, AL (US); Adam Lewis, Madison, MS (US)

(73) Assignee: ALEVIO, LLC, Birmingham, AL (US)

( * ) Notice: Subject to any disclaimer, the term of this patent is extended or adjusted under 35 U.S.C. 154(b) by 171 days.

(21) Appl. No.: 16/657,592

(22) Filed: Oct. 18, 2019

Related U.S. Application Data

(63) Continuation of application No. 14/459,106, filed on Aug. 13, 2014, now abandoned.

(51) Int. Cl.
*A61B 17/86* (2006.01)
*A61B 17/56* (2006.01)
*A61B 17/16* (2006.01)
*A61B 17/70* (2006.01)

(52) U.S. Cl.
CPC ........ *A61B 17/864* (2013.01); *A61B 17/1635* (2013.01); *A61B 17/70* (2013.01); *A61B 2017/564* (2013.01)

(58) Field of Classification Search
CPC ............................ A61B 17/863; A61B 17/864
See application file for complete search history.

(56) References Cited

U.S. PATENT DOCUMENTS

| | | | | |
|---|---|---|---|---|
| 2013/0018427 | A1* | 1/2013 | Pham | A61B 17/8695 606/301 |
| 2014/0236242 | A1* | 8/2014 | Robinson | A61B 17/8605 606/279 |
| 2014/0257409 | A1* | 9/2014 | Reed | A61B 17/8625 606/304 |

* cited by examiner

*Primary Examiner* — Samuel S Hanna
(74) *Attorney, Agent, or Firm* — C. Brandon Browning; Maynard, Cooper & Gale, PC

(57) ABSTRACT

A bone screw and method of using the same for immobilizing a joint, the bone screw including a screw head, an elongate shaft having a threaded outer wall and a helically-shaped slot extending through the outer wall and longitudinally along the shaft. The slot extends longitudinally along a middle section of the threaded outer wall, terminating short of the proximal and distal ends of the shaft, or the slot extends through the distal end and/or to the proximal end of the shaft immediately adjacent to the screw head. The slot includes a cutting edge that is arranged to engage bone when the screw advances therethrough for cutting away a portion of the bone. A reservoir is located within the elongate shaft for collecting bone that is cut away or removed by the cutting edge.

5 Claims, 7 Drawing Sheets

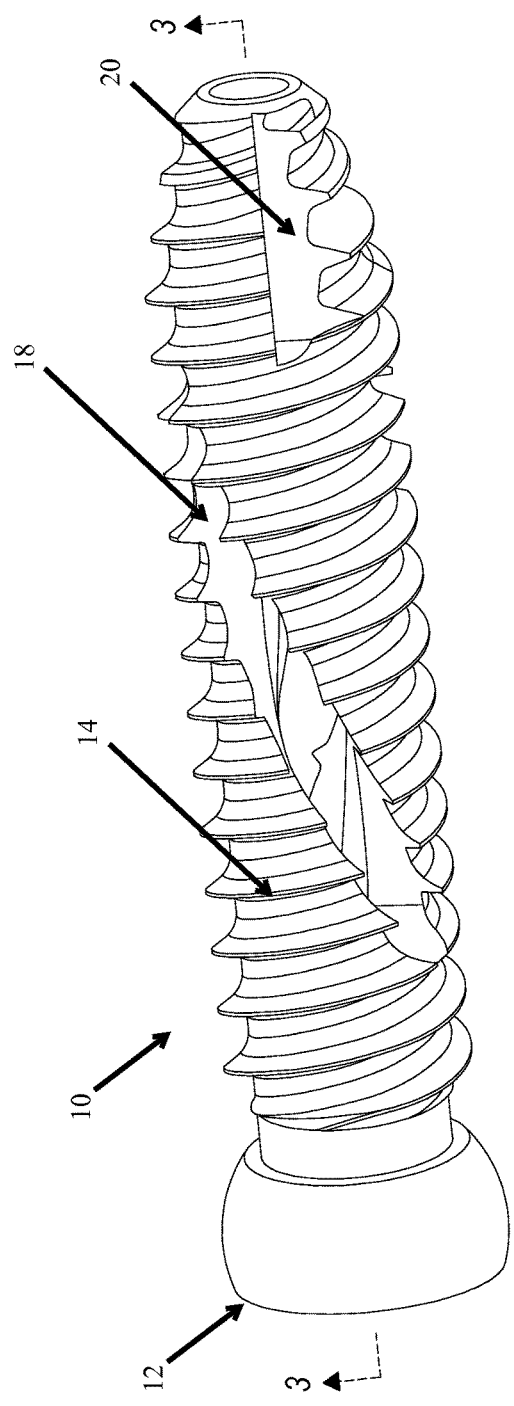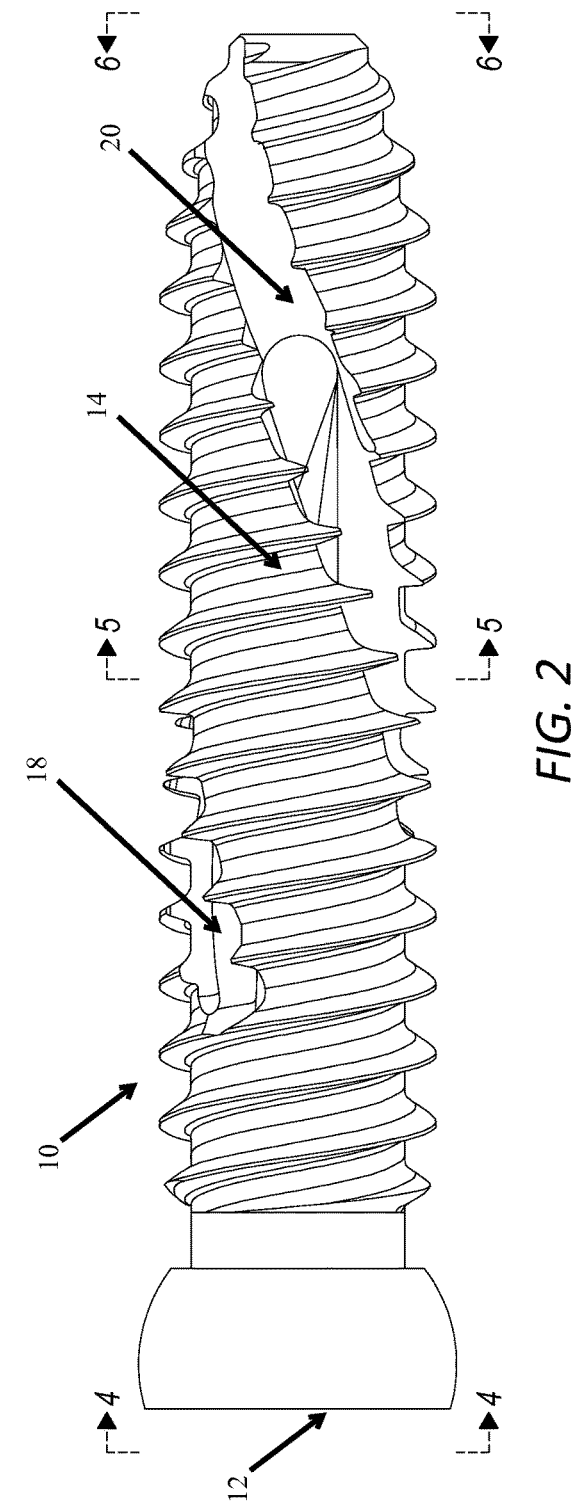
FIG. 1
FIG. 2

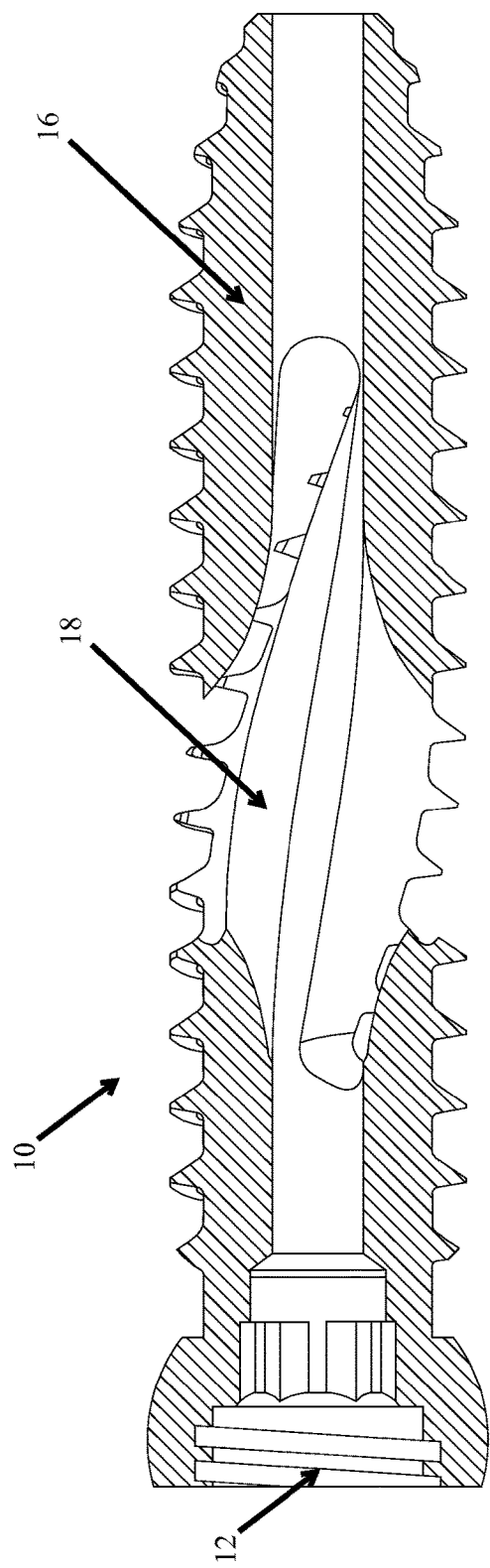
FIG. 3
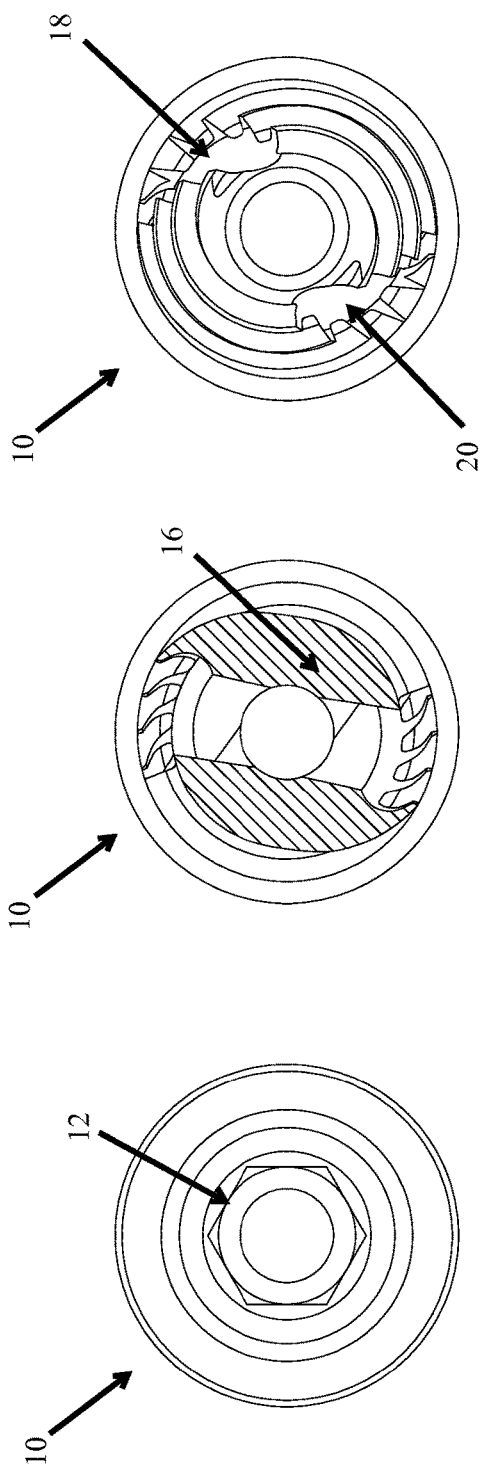
FIG. 4
FIG. 5
FIG. 6

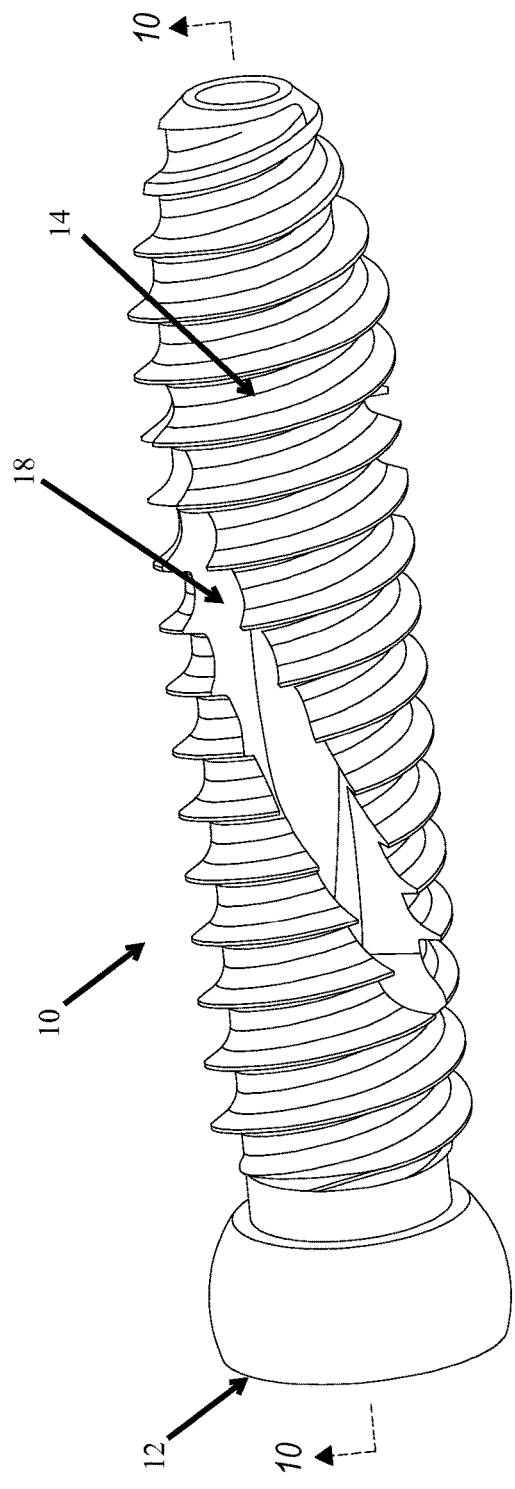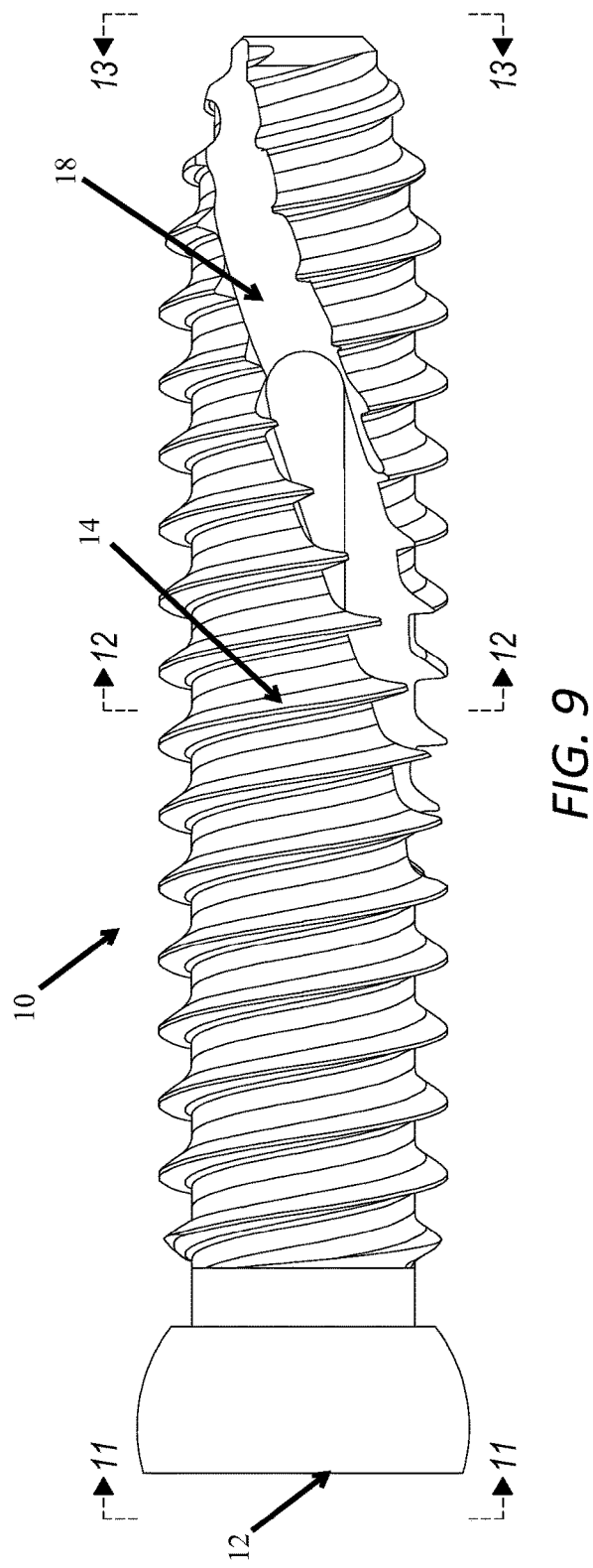
FIG. 8
FIG. 9

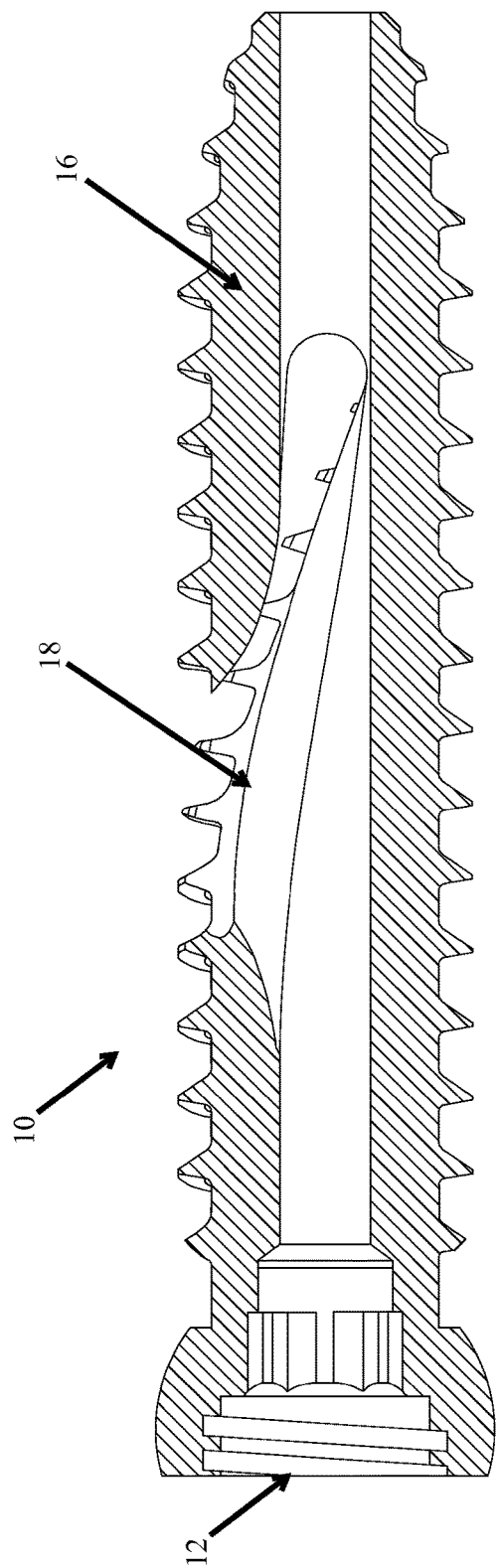
FIG. 10
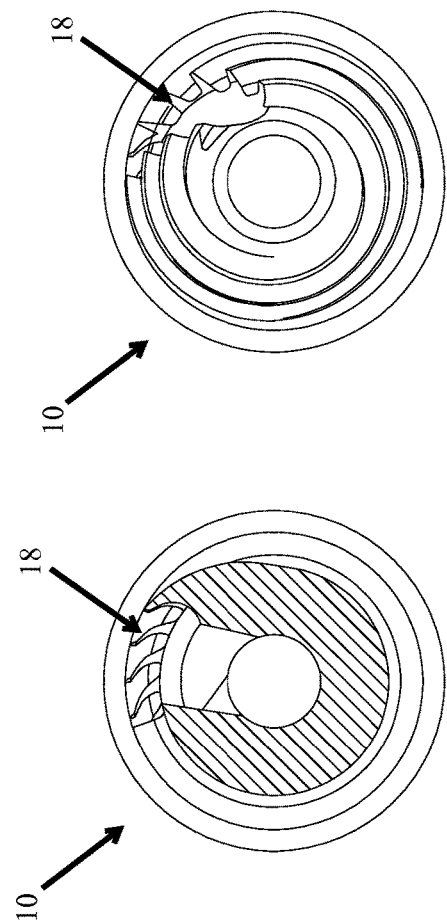
FIG. 13
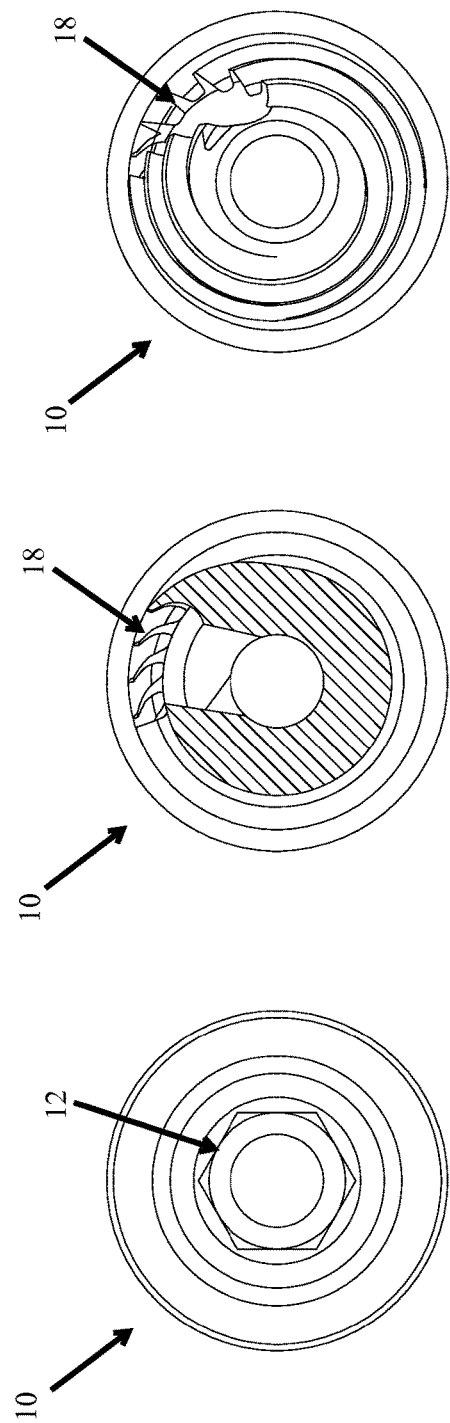
FIG. 12
FIG. 11

BONE SCREW AND METHOD OF USING SAME

RELATED REFERENCES

This application is a continuation of U.S. application Ser. No. 14/459,106, filed on Aug. 13, 2014, titled "Bone Screw and Method of Using Same," the entire contents of which are incorporated herein.

FIELD OF INVENTION

The present invention relates to a bone screw. More particularly, the present invention relates to a bone screw configured for harvesting bone and a method of using the same for immobilizing a joint.

BACKGROUND OF INVENTION

A bone screw is an implant inserted into the bone and can be used to immobilize fractured bone segments to aid in the healing process, as an adjunct to spine fusion surgery to help hold implants in place, and to immobilize damaged or diseased joints. The sacrum, for example, is a large, triangular bone at the base of the lumbar spine, where it connects with the L5 vertebra and is flanked by two hip bones, the left and right ilium. The sacrum connects to the left and right ilium via joints known as sacroiliac joints, which function to transmit force from the spine to the lower extremities. Sacroiliac joints, however, can degenerate due to aging, trauma, and certain diseases, such as degenerative sacroiliitis and inflammatory sacroiliitis. Fusion of the sacroiliac joint may be used to treat pain associated with such degeneration. A need exists for improved implants, such as bone screws, to assist with sacroiliac joint fusion as well as other diseases and conditions requiring the immobilization of fractured bone segments and damaged or diseased joints.

SUMMARY OF INVENTION

The present invention is directed to a bone screw and method of using same for immobilizing a joint. According to one aspect of the invention, there is provided a bone screw including a head, an elongate shaft having a threaded outer wall and a helically-shaped first slot extending through the outer wall and longitudinally along the shaft. The first slot may extend longitudinally along a middle section of the threaded outer wall, terminating short of the proximal and distal ends of the shaft, or the first slot may extend through the distal end and/or to the proximal end of the shaft immediately adjacent to the screw head. At least a portion of the first slot includes a first cutting edge that is arranged to engage bone when the screw advances therethrough for cutting away a portion of the bone. The first cutting edge may extend the entire length of the first slot or be intermittently represented along the first slot. A reservoir is located within the elongate shaft. The reservoir is in fluid communication with the first slot and is arranged to collect the bone that is cut away or removed by the first cutting edge. An opening may be included through a distal end of the shaft and about the longitudinal axis of the shaft, the opening being in fluid communication with the reservoir. When the screw head includes an opening therethrough, the openings in the distal end of the shaft and the screw head may be fluidly coupled via the reservoir. The screw may also include a helically-shaped second slot having a second cutting edge in fluid communication with the reservoir. When the second slot is included, it is preferably located 180° from the first slot.

According to another aspect of the invention, there is provided a method of anchoring a screw within a bone. The method includes the steps of providing a screw having a threaded outer wall including a curved slot therethrough, the curved slot being defined at least in part by a cutting edge, engaging the screw with a first bone, rotating the screw and thereby cutting a portion of bone away from the first bone and collecting the portion of bone within a reservoir in the screw. By collecting and storing the portion of bone in the reservoir, growth of the first bone into the reservoir is promoted such that, ultimately, the first bone and the portion of bone collected in the reservoir become integral. To further promote ingrowth of the first bone into the reservoir, a bone stimulant may be introduced into the reservoir through an opening in a head of the screw.

In those instances where it is desired to immobilize a joint, the screw may be advanced through the first bone, across the joint and into a second bone. An exemplary joint is the sacroiliac joint where the screw may be anchored within an ilium bone and a sacrum bone. Further, when it is desired that a joint be compressed or adjacent bones be drawn together, the threaded outer wall may have a first section including threads with a first pitch and a second section including threads with a second pitch that is different than the first pitch. In particular, the first section may be located along a distal section of the shaft and include threads having a pitch that is less than the pitch of the threads of the second section, which is located at a proximal end of the shaft. This arrangement allows the shaft to advance more quickly through the first bone than through the second bone so that the first bone and the second bone are drawn together. Alternatively, a similar effect can be accomplished when the proximal end of the shaft is smooth, including no threads.

When the screw is used to immobilize a joint, the bone cut away and collected within the reservoir from the first bone and the second bone promotes integral coupling of the first bone and the second bone via bone growth through the reservoir. In essence, a bridge of integrally-formed bone extends to and between the first bone and the second bone via the reservoir.

BRIEF DESCRIPTION OF THE DRAWINGS

FIG. 1 is a perspective view of a bone screw in accordance with a preferred embodiment of the present invention.

FIG. 2 is an elevational view of the bone screw of FIG. 1.

FIG. 3 is a sectional view of the bone screw of FIG. 1 along line 3-3.

FIG. 4 is a plan view of a proximal end of the bone screw of FIG. 1.

FIG. 5 is a sectional view of the bone screw of FIG. 1 along line 5-5.

FIG. 6 is a plan view of a distal end of the bone screw of FIG. 1.

FIG. 8 is a perspective view of a bone screw in accordance with another preferred embodiment of the present invention.

FIG. 9 is an elevational view of the bone screw of FIG. 8.

FIG. 10 is a sectional view of the bone screw of FIG. 8 along line 10-10.

FIG. 11 is a plan view of a proximal end of the bone screw of FIG. 8.

FIG. 12 is a sectional view of the bone screw of FIG. 8 along line 12-12.

FIG. 13 is a plan view of a distal end of the bone screw of FIG. 8.

DETAILED DESCRIPTION OF PRESENTLY PREFERRED EMBODIMENTS

Before the present compositions, articles, devices, and/or methods are disclosed and described, it is to be understood that they are not limited to specific methods unless otherwise specified, or to particular reagents unless otherwise specified, and as such may vary. It is also to be understood that the terminology as used herein is used only for the purpose of describing particular embodiments and is not intended to be limiting.

A. Definitions

In this specification, and in the claims that follow, reference is made to a number of terms that shall be defined to have the following meanings:

As used herein, the singular forms "a," "an," and "the" include plural referents unless the context clearly indicates otherwise. Thus, for example, reference to "a bone screw" includes two or more such bone screws, and the like.

As used herein, the terms "bone screw" and "screw" may be used interchangeably.

As used herein, the term "joint" refers to the region of contact between two or more bones. For example, a joint may refer to the acromioclavicular (AC) joint between the acromion and the clavicle.

As used herein, the term "subject" is any animal, including primates, in particular humans, and other mammals including, but not limited to, equines, cattle, swine, and sheep; and poultry and pets in general.

As used herein, the term "surgeon" includes any treating physician or any treatment professional under the direction of a surgeon or other treating physician.

As used herein, the terms "treat", "treatment" or "treating" include any desirable effect on the symptoms or pathology of a disease or condition, and may include even minimal reductions in one or more measurable markers of the disease or condition being treated. "Treatment" does not necessarily indicate complete eradication or cure of the disease or condition, or associated symptoms thereof.

B. Bone Screw and Methods of Use

Figure 7:
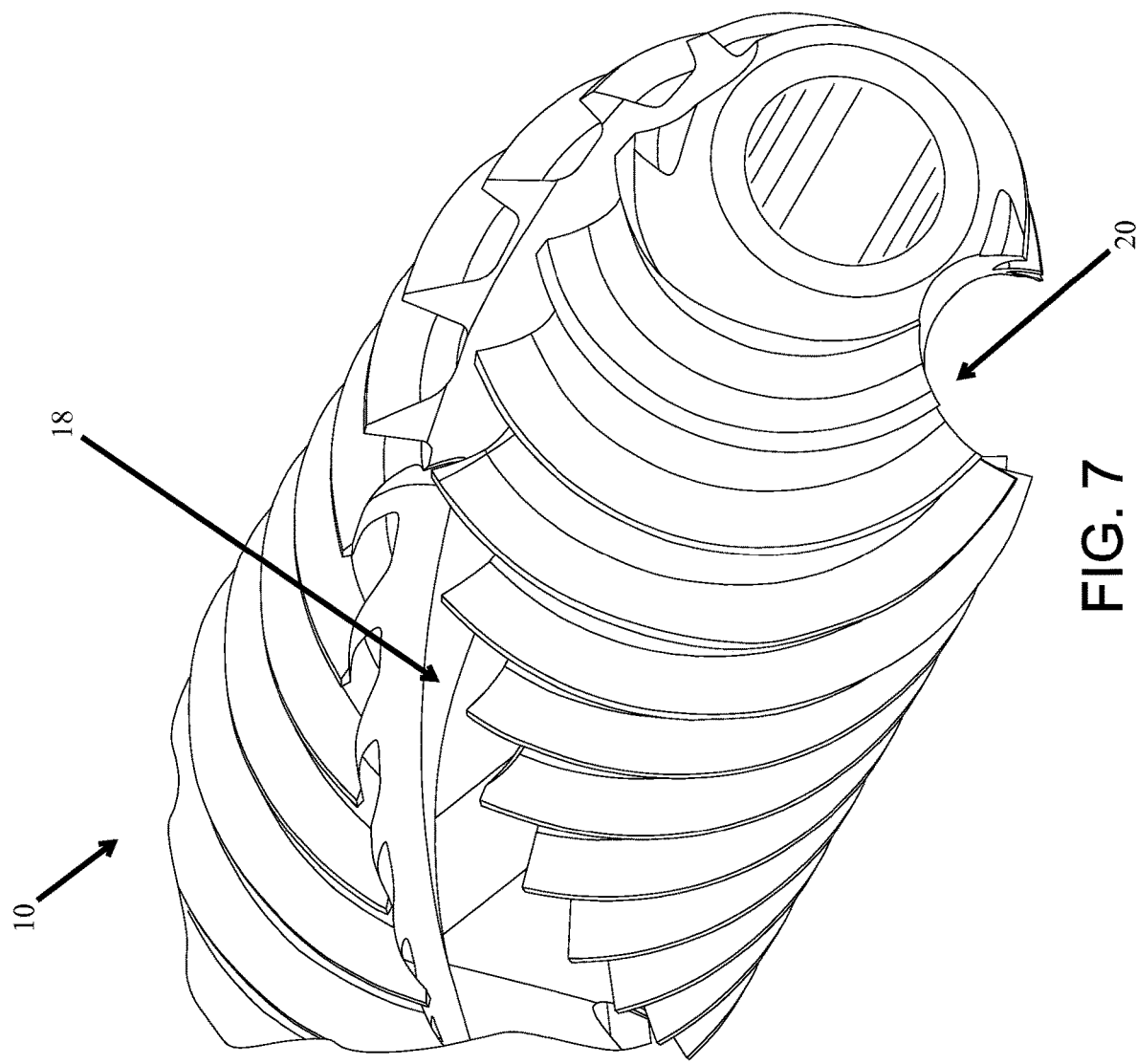
FIG. 7 is a perspective view of the distal end of the bone screw of FIG. 1.
Figure 14:
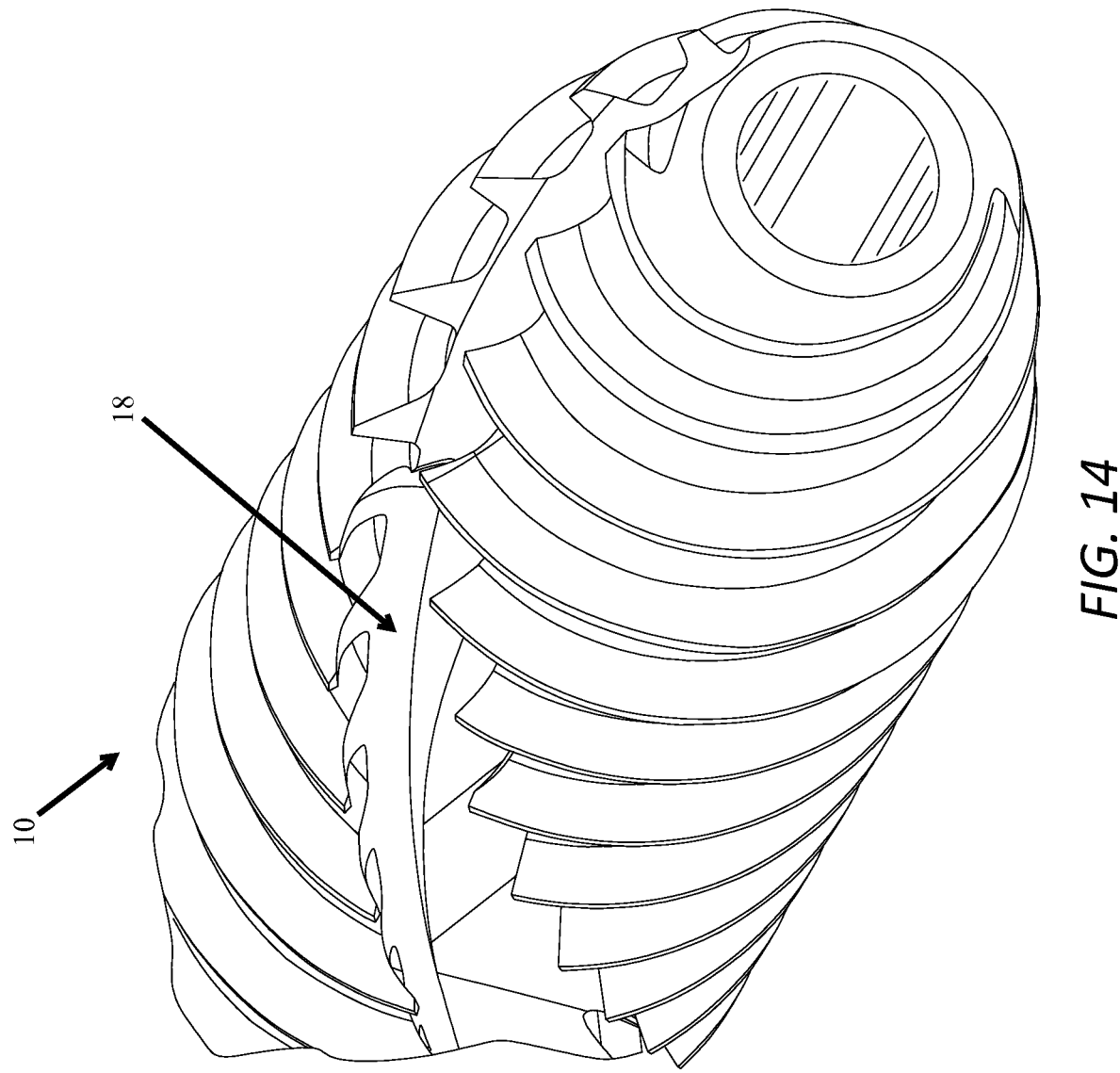
FIG. 14 is a perspective view of the distal end of the bone screw of FIG. 8.
Figure 15:
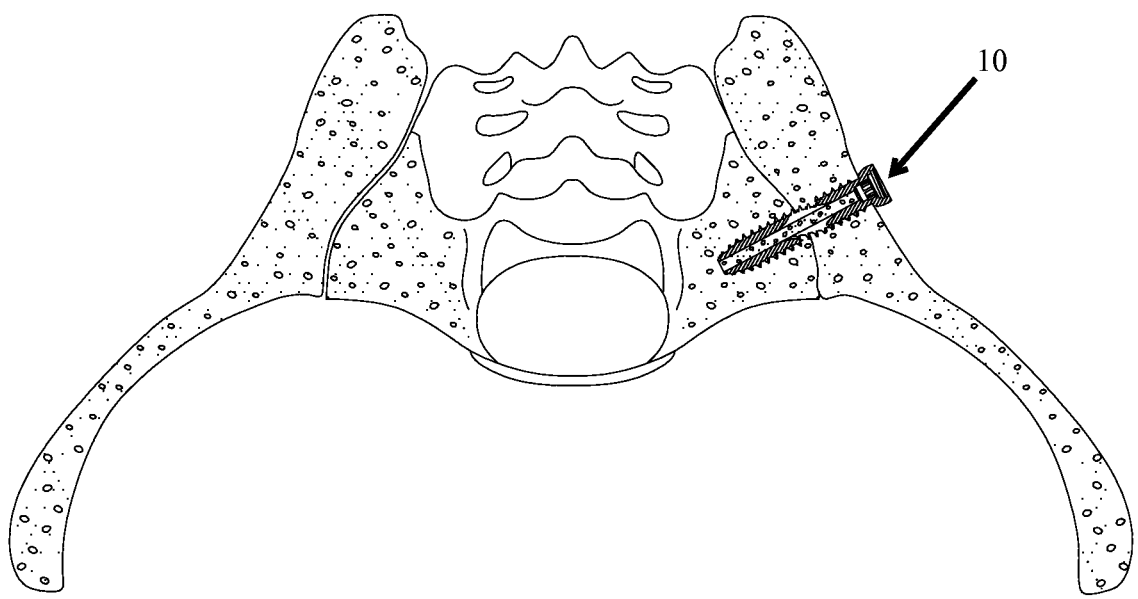
FIG. 15 is a partial sectional view of a sacroiliac joint illustrating the bone screw of FIG. 1 through and across the joint of an ilium bone and a sacrum bone.

The present invention is directed to bone screws and methods of using the same for immobilizing a joint, and more particularly, for cutting away portions of bone located adjacent to the joint and collecting and storing the bone portions in a bone screw reservoir thereby creating a pathway for promoting bone growth into and through the bone screw. The reservoir may be non-smooth, for example roughened or porous, and may include a bone ingrowth surface. The non-smooth surface can be provided by techniques known to those skilled in the art including, but not limited to, acid etching, laser deformation, and abrasive media blasting, such as sand blasting. FIGS. 1 through 7 depict a first embodiment of a bone screw 10 in accordance with a preferred embodiment of the present invention. FIGS. 8 through 14 depict a second embodiment of a bone screw 10 in accordance with another preferred embodiment of the present invention, where like features share like numbers with FIGS. 1 through 7. FIG. 15 depicts a sacroiliac joint that is fused using the bone screw 10. The bone screw 10 is comprised of a hard and durable material, such as titanium, which is medically acceptable for insertion into the body and possesses sufficient strength to withstand the torque and tension exerted upon the bone screw 10 during and after placement. In one embodiment, the bone screw 10 is comprised of medical grade titanium, such as TI6AL4V. In other embodiments, the bone screw 10 may be comprised of commercially pure titanium and its alloys, ASTM material, cobalt chrome, tantalum, ceramic, various surgical grade plastics, plastic composites, carbon fiber composites, coral, and/or artificial materials which are at least in part bioresorbable.

Referring to FIGS. 1 through 7, bone screw 10 includes a head 12, an elongate shaft 14 having a threaded outer wall 16, a helically-shaped first slot 18 extending through outer wall 16 and longitudinally along shaft 14 and a helically-shaped second slot 20 extending through outer wall 16, longitudinally along shaft 14 and 180° from first slot 18.

The head 12 is configured with a hex socket, as shown in FIGS. 4 and 11, to accommodate a driver as will be hereinafter further explained in connection with a description of a method in which the bone screw 10 is inserted into bone. In other embodiments, the head 12 may be configured with other types of sockets known to those skilled in the art.

The first slot 18 may extend longitudinally along a middle section of the threaded outer wall 16, terminating short of the proximal and distal ends of the shaft 14, or the first slot 16 may extend through the distal end and/or to the proximal end of the shaft 14 immediately adjacent to the screw head 12. At least a portion of the first slot 18 includes a first cutting edge that is arranged to engage bone when the screw advances therethrough for cutting away a portion of the bone. The first cutting edge may extend the entire length of the first slot 18 or be intermittently represented along the first slot 18. A reservoir is located within the elongate shaft 14. The reservoir is in fluid communication with the first slot 18 and arranged to collect the bone that is cut away or removed by the first cutting edge. An opening may be included through a distal end of the shaft 14 and about the longitudinal axis of the shaft 14, the opening being in fluid communication with the reservoir. When the screw head 12 includes an opening therethrough, the openings in the distal end of the shaft 14 and the screw head 12 may be fluidly coupled via the reservoir. The bone screw 10 may also include a helically-shaped second slot 20 having a second cutting edge in fluid communication with the reservoir. When the second slot 20 is included, it is preferably located 180° from the first slot 16, as shown in FIGS. 5 and 6.

Referring to FIGS. 8 through 14, bone screw 10 includes a head 12, an elongate shaft 14 having a threaded outer wall 16, and one helically-shaped slot 18 extending through outer wall 16 and longitudinally along shaft 14. The slot 18 may extend longitudinally along a middle section of the threaded outer wall 16, terminating short of the proximal and distal ends of the shaft 14, or the slot 18 may extend through the distal end and/or to the proximal end of the shaft 14 immediately adjacent to the screw head 12. At least a portion of the slot 18 includes a cutting edge that is arranged to engage bone when the bone screw 10 advances therethrough for cutting away a portion of the bone. The cutting edge may extend the entire length of the slot 18 or be intermittently represented along the slot 18. A reservoir is located within the elongate shaft 14. The reservoir is in fluid communication with the slot 18 and is arranged to collect the bone that is cut away or removed by the cutting edge. An opening may be included through a distal end of the shaft 14 and about the longitudinal axis of the shaft 14, the opening being in fluid communication with the reservoir. When the screw head 12 includes an opening therethrough, the openings in the distal end of the shaft 14 and the screw head 12 may be fluidly coupled via the reservoir.

FIG. 15 depicts a partial sectional view of a sacroiliac joint where bone screw 10 of FIG. 1 connects an ilium bone and a sacrum bone across the joint. The bone screw 10 is advanced into the bone leaving only a head 12 exposed. The reservoir of the bone screw 10 contains bone, collected by a helically-shaped first slot 18 and a helically-shaped second slot 20 as the bone screw 10 advanced through the ilium bone and the sacrum bone. Although the bone screw 10 represented in FIG. 15 has two helically-shaped slots, in other embodiments, the bone screw 10 has a single helically-shaped slot 18, for example as depicted in FIGS. 8-14. In other embodiments, the bone screw 10 connects combinations of bone other than an ilium bone and a sacrum bone. In other embodiments, at least two bone screws 10 connect the same two or more bones.

Further, when it is desired that a joint be compressed or adjacent bones be drawn together, the threaded outer wall 16 may have a first section including threads with a first pitch and a second section including threads with a second pitch that is different than the first pitch. In particular, the first section may be located along a distal section of the shaft 14 and include threads having a pitch that is less than the pitch of the threads of the second section, which is located at a proximal end of the shaft 14, allowing the shaft 14 to advance more quickly through the first bone than through the second bone so that the first bone and the second bone are drawn together. In another embodiment, the proximal end of the shaft 14 is smooth, including no threads, allowing the shaft 14 to advance more quickly through the first bone than through the second bone so that the first bone and the second bone are drawn together.

According to another aspect of the invention, there is provided a surgical method of anchoring a bone screw 10 within a bone in a subject. In certain embodiments, the bone screw 10 may be used to treat a subject requiring bone fusion, such as a subject undergoing lumbar spinal fusion surgery. The method includes the steps of a surgeon performing an incision in a subject, engaging a bone screw 10 with a first bone, rotating the bone screw 10 and thereby cutting a portion of bone away from the first bone and collecting the portion of such bone within a reservoir in the bone screw 10. In one embodiment, the surgeon uses a guidance tool, such as a sleeve, to guide the bone screw 10 to the desired location. In one embodiment, the surgeon scores or otherwise prepares the bone prior to inserting the bone screw 10 into the bone. The surgeon rotates and screws the bone screw 10 into bone using a tool having a hex driver extending therefrom which is connectable to the hex socket on the head 12 of the bone screw 10. In other embodiments, driver and socket combinations other than hex form may be used.

The bone is collected and stored in the reservoir, promoting growth of the first bone into the reservoir such that, ultimately, the first bone and the portion of bone collected in the reservoir become integral. In one embodiment, an osteogenic factor is introduced into the reservoir through an opening in a head 12 of the bone screw 10 to further promote ingrowth of bone into the reservoir. Osteogenic factors may include, but are not limited to, bone morphogenetic proteins, such as BMP-2, BMP-4, and BMP-7, osteogenin, bone osteogenic protein (BOP), IGF-II, TGF-beta, mesenchymal stem cells, blood or blood fractions, bone marrow or bone marrow fractions, and/or other sources of cells or other beneficial tissue components derived from the subject or another suitable animal source.

In one embodiment, there is provided a method for immobilizing a joint, the method including the advancing at least one bone screw 10 through a first bone, across a joint and into a second bone by rotation of the bone screw 10. An exemplary joint is the sacroiliac joint where at least one bone screw 10 may be anchored within an ilium bone and a sacrum bone, but in other embodiments the bone screw 10 may be anchored into different bone joints.

When the bone screw 10 is used to immobilize a joint, the bone is cut away and collected within the reservoir from the first bone and the second bone promotes integral coupling of the first bone and the second bone via bone growth through the reservoir. In essence, a bridge of integrally-formed bone extends to and between the first bone and the second bone via the reservoir.

It is claimed:

1. A method of anchoring a screw within a bone comprising:
   providing a screw with a screw head, a distal end including a tapered distal tip, and an elongate shaft extending to and between the screw head and the distal end, the elongate shaft including,
   a proximal end immediately adjacent to the screw head,
   an outer shaft wall surface including helical threads extending radially outward therefrom along the outer shaft wall surface from the proximal end to the distal end,
   an inner shaft wall surface that defines a reservoir that extends along a longitudinal axis of the elongate shaft,
   a first helical-shaped groove formed in the outer wall surface that extends from the proximal end to and through the distal end and intersecting the helical threads, the first helical-shaped groove defining a proximal helical-shaped concave surface at the proximal end forming an undercut and a distal helical-shaped concave surface at the distal end forming an undercut, each of the proximal and distal helical-shaped concave surfaces separates the first helical-shaped groove from the reservoir,
   a second helical-shaped groove formed in the outer wall surface arranged 180° to the first helical-shaped groove that extends from the proximal end to and through the distal end and intersecting the helical threads, said second helical-shaped groove defines a proximal helical-shaped concave surface at the proximal end forming an undercut and a distal helical-shaped concave surface at the distal end forming an undercut, each of the proximal and distal helical-shaped concave surfaces separates the second helical-shaped groove from the reservoir,
   a first helical-shaped elongated opening located in the first helical-shaped groove, that extends through the inner shaft wall surface and from adjacent to the proximal end to a first position adjacent to the distal end between the proximal and distal helical-shaped concave surfaces of the first helical-shaped groove, and a second helical-shaped elongated opening located in the second helical-shaped groove, that extends through the inner shaft wall surface and from adjacent to the proximal end to a second position adjacent to the distal end between the proximal and distal helical-shaped concave surfaces of the second helical-shaped groove, wherein each of the first and second helical-shaped grooves has a cutting edge extending an entire length of a corresponding helical-shaped groove of the first and second helical-shaped grooves, engaging the distal end of the screw with a first bone, rotating the screw and thereby cutting, by the cutting edges, a first bone portion away from the first bone and a second bone portion away from a second bone, the second bone is separated from the first bone by a joint, directing the first and second bone portions by the first and second helical-shaped grooves through the first and second helical-shaped openings, respectively, and into the reservoir, and fully inserting the screw into the first bone, across the joint and into the second bone, such that the screw head is seated against the first bone, and the first elongated helical-shaped opening and the second elongated helical-shaped opening are arranged directly against the joint and a first portion of the first bone adjacent to the joint and a second portion of the second bone adjacent to the joint.

2. The method of claim 1, wherein the first bone and the second bone become integrally coupled via bone growth through the reservoir, the first helical-shaped opening and the second helical-shaped opening that is promoted by the presence of the first and second bone portions stored in the reservoir.

3. A method of anchoring a screw within a bone comprising:

providing a screw with a screw head, a proximal end adjacent to the screw head, a distal end including a tapered distal tip, and an elongate shaft extending to and between the screw head and the distal end, the elongate shaft including, an outer shaft wall including helical threads extending radially outward therefrom along the outer shaft wall surface from the proximal end to the distal end, an inner shaft wall surface that defines a reservoir, a helical-shaped groove formed in the outer wall surface, that extends from the proximal end to and through the distal end and intersecting the helical threads, wherein the helical-shaped groove defines a proximal helical-shaped concave surface at the proximal end forming an undercut and a distal helical-shaped concave surface at the distal end forming an undercut, wherein the proximal and distal helical-shaped concave surfaces separate the helical-shaped groove from the reservoir, and an elongated helical-shaped opening located in the helical-shaped groove, that extends through the inner shaft wall surface and from adjacent to the proximal end to a position adjacent to the distal end between the proximal and distal helical-shaped concave surfaces of the helical-shaped groove, wherein the helical-shaped groove has a cutting edge extending a length of the helical-shaped groove, rotating the screw and thereby cutting, with the cutting edge, a first bone portion away from a first bone and a second bone portion away from a second bone, the second bone is separated from the first bone by a joint, directing the first and second bone portions through the elongated helical-shaped opening into the reservoir, and fully inserting the screw into the first bone, across the joint and into the second bone such that the screw head is seated against the first bone, and the elongated helical-shaped opening is arranged directly against the joint and a first portion of the first bone adjacent to the joint and a second portion of the second bone adjacent to the joint.

4. A method of anchoring a screw within a bone comprising:

providing a screw with a screw head, a distal end including a tapered distal end, and an elongate shaft extending to and between the screw head and the distal end, the elongate shaft including, a proximal end adjacent to the screw head, a first length that extends to and between the screw head and the distal end, an outer shaft wall surface including helical threads extending radially outward therefrom along the outer shaft wall surface from the proximal end to the distal end, an inner shaft wall surface that defines a reservoir, a helical-shaped groove extending from the proximal end to and through the distal end and intersecting the helical threads, the helical-shaped groove defining a proximal helical-shaped concave surface at the proximal end forming an undercut and a distal helical-shaped concave surface at the distal end forming an undercut, wherein the proximal and distal helical-shaped concave surfaces separate the first helical-shaped groove from the reservoir, and a helical-shaped slot located in the helical-shaped groove, that extends through the inner wall surface and from adjacent to the proximal end to a position adjacent to the distal end between the proximal and distal helical-shaped concave surfaces of the helical-shaped groove, wherein the helical-shaped groove defines a cutting edge extending a length of the helical-shaped groove, rotating the screw and thereby cutting, by the cutting edge, a first bone portion away from a first bone and a second bone portion away from a second bone, the second bone is separated from the first bone by a joint, directing the first and second bone portions through the elongated helical-shaped slot into the reservoir, and fully inserting the screw into the first bone, across the joint and into the second bone, such that the screw head is seated against the first bone, and the helical-shaped slot is arranged directly against the joint and a first portion of the first bone adjacent to the joint and a second portion of the second bone adjacent to the joint.

5. The method of claim 4 wherein the helical-shaped opening does not extend through the distal end of the screw.

\* \* \* \* \*